United States Patent [19]
Doan

[11] Patent Number: 5,466,253
[45] Date of Patent: Nov. 14, 1995

[54] CRUSH RESISTANT MULTI-CONDUCTOR LEAD BODY

[75] Inventor: Phong D. Doan, Stevenson Ranch, Calif.

[73] Assignee: Pacesetter, Inc., Sylmar, Calif.

[21] Appl. No.: 54,571

[22] Filed: Apr. 27, 1993

[51] Int. Cl.⁶ ..................................................... A61B 5/04
[52] U.S. Cl. ..................................................... 607/122
[58] Field of Search .................................. 607/116, 122, 607/123, 119; 128/642

[56] References Cited

U.S. PATENT DOCUMENTS

| | | | |
|---|---|---|---|
| 4,198,991 | 4/1980 | Harris | 607/122 |
| 4,559,951 | 12/1985 | Dahl et al. | 128/642 |
| 4,573,480 | 3/1986 | Hirschberg | 607/119 |
| 4,840,186 | 6/1989 | Lekholm et al. | 607/116 |

OTHER PUBLICATIONS

Fyke, F. Earl III, "Infraclavicular Lead Failure: Tarnish on a Golden Rule," PACE, vol. 16, pp. 373–376 (Mar., Part I, 1993).

Jacobs, Donald M. et al., "Anatomical and Morphological Evaluation of Pacemaker Lead Compression," PACE, vol. 16, pp. 434–444 (Mar., Part I, 1993).

Magney, Jean E., et al., "Anatomical Mechanisms Explaining Damage to Pacemaker Leads, Defibrillator Leads, and Failure of Central Venous Catheters Adjacent to the Sternoclavicular Joint," PACE, vol. 16, pp. 445–457, (Mar., Part I, 1993).

Primary Examiner—William E. Kamm
Assistant Examiner—Scott M. Getzow
Attorney, Agent, or Firm—Harold C. Schloss

[57] ABSTRACT

An implantable pacing lead having a flexible insulative material injected into the passageway accommodating the electrical conductor(s) to encapsulate the conductor(s) for at least the portion of the lead body most subject to physical damage to in the lead body.

8 Claims, 3 Drawing Sheets

CRUSH RESISTANT MULTI-CONDUCTOR LEAD BODY

BACKGROUND OF THE INVENTION

This invention relates generally to an implantable pacing lead for use with a cardiac pacemaker, and more specifically, to a pacing lead having lead body wherein the conductors are protected from being crushed by the subclavian bone and muscle structure.

Clinical evidence suggests that certain upper extremity activities are contraindicated for persons with permanent pacemakers because they require movements that can cause damage to leads. Currently, leads used in cardiac stimulation are often implanted transvenously or transthoracically with the result that the lead body can be physically crushed by either bones (i.e. "first rib-clavicle") or by tissue (costoclavicular ligament complex, subclavius muscle) and by anchoring sleeves which are tied-down so tightly that the lead body can be crushed or damaged. The result of these crushing or constrictive stresses can be severe damage to the conductors within the lead body which, in turn, can result in failed conductors and/or failed insulation.

Some leads and central venous catheters placed by percutaneous subclavian venipuncture have developed a number or problems that are apparently associated with the costoclavicular region near the superior thoracic aperture. Catheters or leads implanted by subclavian venipuncture can be damaged by bony compression or impingement by dense tissues as the lead passes through the vein beneath the clavicle, over the first rib, and into the thorax just lateral to the sternoclavicular joint. Studies suggest that an overriding clavicle can crush leads against the first rib with a "pincher-like" action. Leads can also be compressed within the costoclavicular ligament complex.

Conductor mechanical damage including fractures and/or insulation breaks occur in about 2% to 3% of all implanted leads. In patients who are not pacemaker dependent, the event is usually not life-threatening, but can require invasive corrective procedures with potential complications. Mechanical damage is defined as coil deformation, coil fracture, mechanically induced insulation breaches, and insulation wear observed individually or in combination. Pacing lead coils under compression are characterized by flattened helical conductors. Fatigue fractures resulting from repeated cyclic compressive loading usually initiate at the outer surface of the coil.

In view of the foregoing, it has been proposed that the percutaneous subclavian venipuncture approach should be abandoned because the incidence of lead fracture in the costoclavicular region is unacceptable. However, it is also recognized that this method of implant has become the standard procedure for the majority of pacemaker lead implants. Accordingly, it would be beneficial to have a lead design which resists rib-clavicle, tissue and suture sleeve imposed mechanical damage, and allows continuation of accepted implanting procedures.

SUMMARY OF THE INVENTION

The present invention is applicable to leads having single or multiple coaxial conductors which are helically wound, as well as for multilumen tubing leads. More specifically, conductors which are confined within and/or separated by two coaxial cylindrical tubings, are coated and encapsulated in a flexible insulative protective material, which minimizes the physical stresses noted above, preventing damage to the conductors and insulation tubing in the lead body. The length of the portion of the lead which includes the protective material is long enough to protect the conductors in the lead body from a point near the connector at the proximal end to a point beyond that portion of the lead which would be stressed by bones, ribs, suture sleeves, etc.

Alternatively, the pacing lead can be formed using a multilumen tube, which is generally an elongated length of silicone tubing having multiple axially aligned channels or lumens extending therethrough. When the multilumen tubing is assembled with other components of the system, the individual conductors are inserted into the lumens of the multilumen tubing, and advanced to their point of interconnection to their respective electrodes at the distal end and electrical connectors at the proximal end. The conductors within the lumens are coated and encapsulated with the flexible insulative protective material.

DETAILED DESCRIPTION OF THE PREFERRED EMBODIMENT

Figure 1:
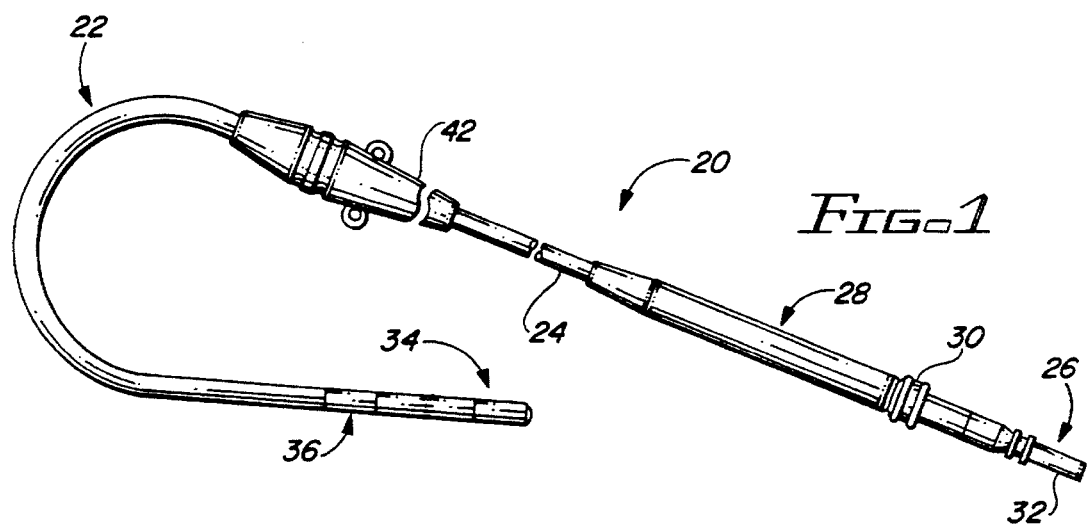
FIG. 1 shows a plan view of a pacing lead of the present invention.

FIG. 1 shows a pacing lead 20. The pacing lead 20 is provided with an elongated lead body 22 which includes a pair of coaxially mounted, helically wound electrical conductors covered with an insulation sheath 24. The sheath 24 is preferably fabricated of silicone rubber, polyurethane or other suitable plastic tubing.

At a proximal end 26 of the pacing lead 20 is a connector assembly 28, which is provided with sealing rings 30 and which carries at least one electrical connector 32. The connector assembly 28 is constructed using known techniques and is preferably fabricated of silicone rubber, polyurethane or other suitable plastic. The electrical connectors 32 are preferably fabricated of stainless steel or other suitable conductive material. At a distal end 34 of the pacing lead 20 is an electrode assembly 36, which may include multiple electrodes or sensors, and which is intended to be implanted into the heart.

Figure 2:
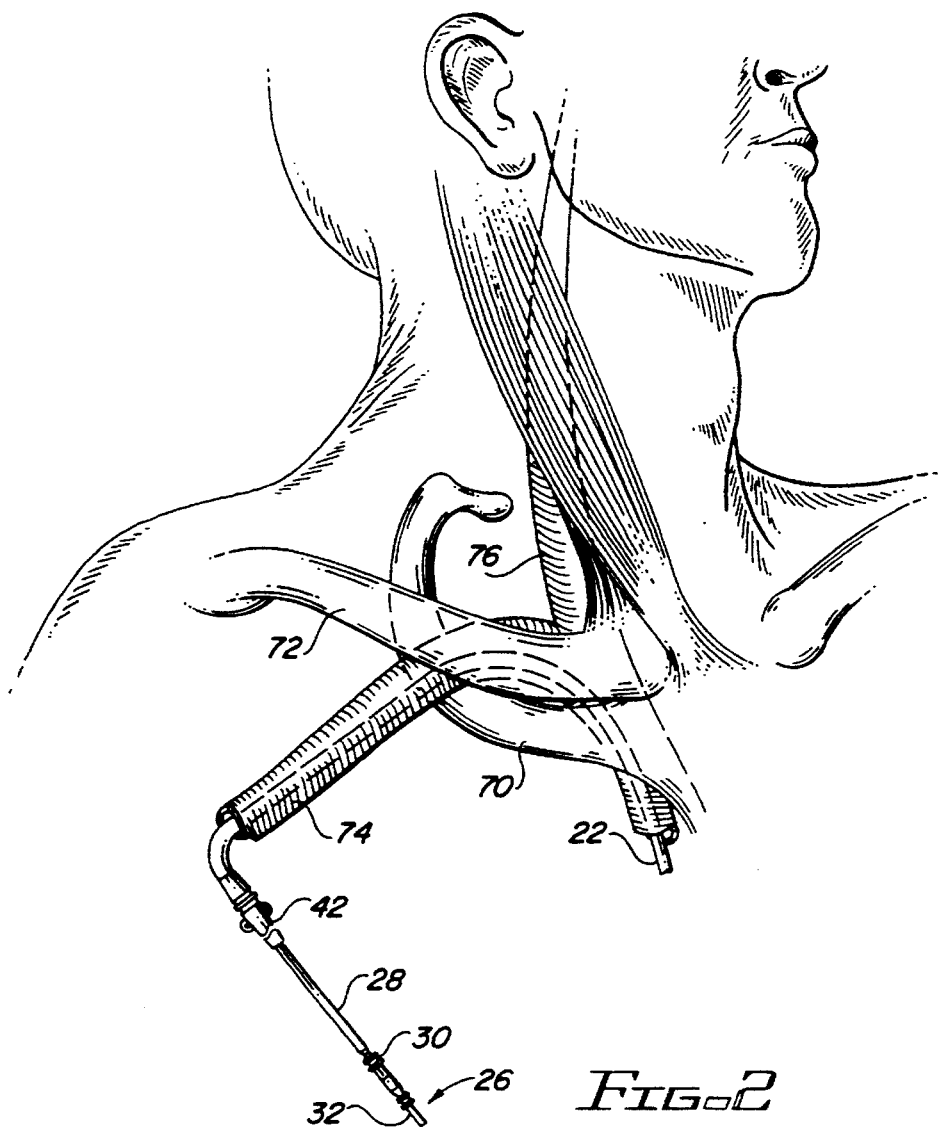
FIG. 2 shows a partially schematic view of the implanted pacing lead in the area of venous insertion, and the proximate skeletal structure.

FIG. 2 illustrates the right side neck-shoulder area of a patient. In FIG. 2, the first rib 70 and right clavicle 72 of the skeletal structure are illustrated. The subclavian vein 74 passes between the first rib 70 and right clavicle 72 before merging with the internal jugular vein 76 and proceeding to the heart (not shown). The pacing lead 20 is inserted into the subclavian vein 74, and extends through the rib 70—clavicle 72 crossing point and down the jugular vein to the heart (not shown). A fixation sleeve 42, which may be either fixed or slidably mounted around lead body 22, serves to stabilize the pacing lead 20 at the site of venous insertion.

Figure 3:
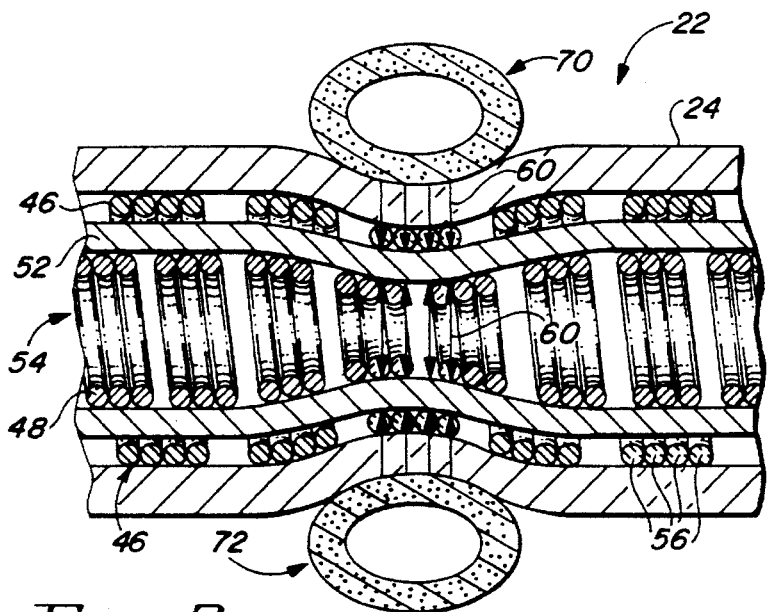
FIG. 3 shows a detailed cutaway axial view of a pacing lead in the area of the subclavian transition.
Figure 4:
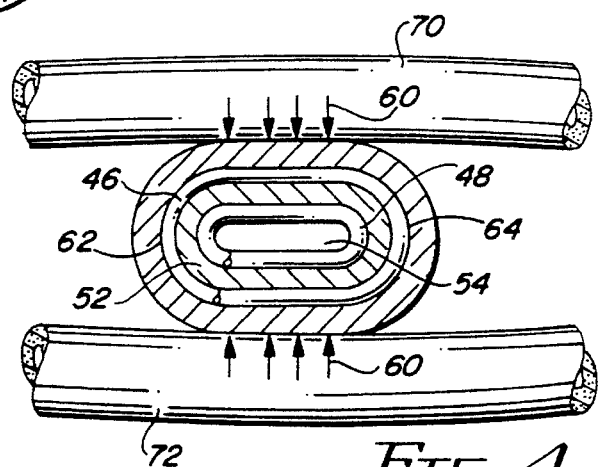
FIG. 4 shows a cross-sectional view of the pacing lead in the area of the subclavian transition.

An enlarged cross-sectional view of a portion of a pacing lead of the prior art in the area of the rib 70—clavicle 72 crossing point is illustrated in the axial view of FIG. 3 and the cross-sectional view of FIG. 4. The lead body includes two conductors 46, 48, separated by insulation tubing 52, all contained within the insulation sheath 24. The spiral winding of the conductor(s) 46, 48 results in a hollow central area 54, and allows the lead body 22 to remain quite flexible. Also, the hollow central area 54 accommodates insertion of a guide wire or stylet (not shown) which is relatively stiff and which allows the doctor to guide and control the implantation of the pacing lead 20.

The axial view in FIG. 3 of the lead body 22, in the area traversing between the first rib 70 and clavicle 72, illustrates the problem addressed by the present invention. In FIG. 3, the outer conductor 46 is illustrated as being contained between the insulation sheath 24 on the outside and an insulation tubing 52 at its inner diameter. The conductor 46, as discussed above, is a helically wound conductor, and therefore the axial view depicts cross-sections of the conductor 46. In addition, it should be understood that the conductor 46 may be made up of a plurality of conductors contained in a bundle 56 to provide redundancy while also retaining flexibility by reducing the cross-sectional thickness which would be required for a single conductor. In addition, the second conductor 48 which is also helically wound is disposed internally of the insulation tubing 52.

The hollow central area must be maintained in order to allow insertion of the stylet to guide implantation. Accordingly, the lead body illustrated in FIGS. 3 and 4 is subject to crushing by the first rib 70 and clavicle 72 during various activities performed by the recipient of the pacing system. The structural forces exerted on the conductor 46, as well as the insulation tubing 52, are identified by the arrows 60. It must also be recognized that the cylindrical structure of the lead body 22 will require that the constriction caused by the first rib 70 and clavicle 72 illustrated in FIG. 2 will cause flattening of the lead body 22, which results in sharp bending deformation of the coil conductors 46 and 48, as illustrated in the cross-sectional view of FIG. 4 at locations 62 and 64.

Figure 5:
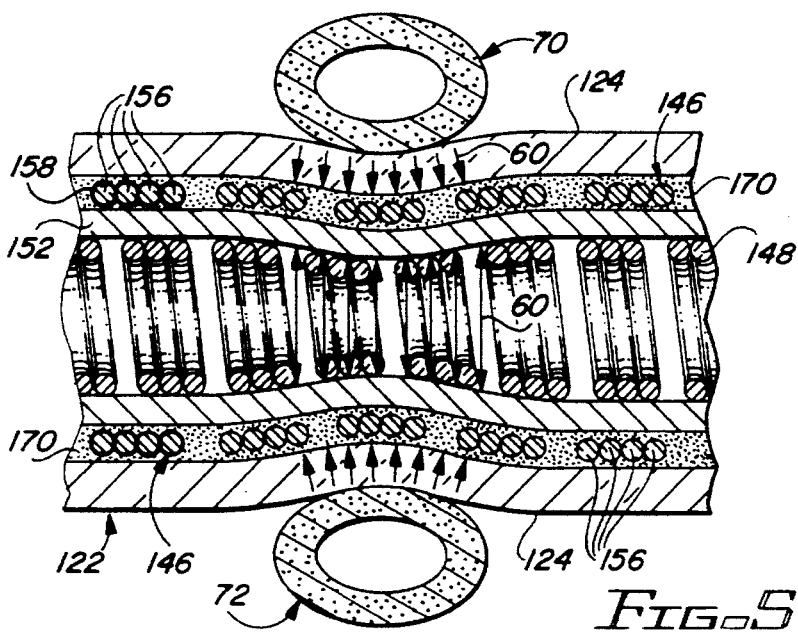
FIG. 5 shows a detailed partial cutaway axial view of a pacing lead according to the present invention in the area of the subclavian transition.
Figure 6:
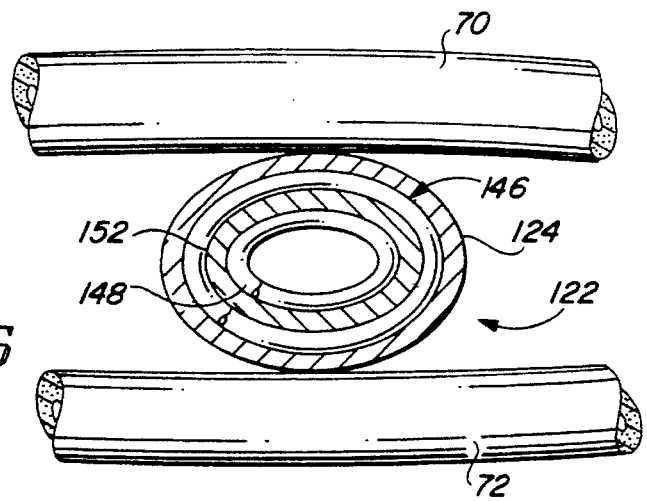
FIG. 6 shows a cross-sectional view of the pacing lead of the present invention in the area of the subclavian transition.

FIGS. 5 and 6 depict an axial and a cross-sectional view through portions of a lead body 122 of the present invention extending between the first rib 70 and clavicle 72, similar to the view of FIG. 4. It is to be understood that the conductors identified in FIGS. 4 and 6 appear solid in cross-section, which results from a tightly wound helix having many turns per inch. Obviously, for helixes with fewer turns per inch, the cross-section would show portions of adjacent windings. As shown in FIG. 5, the lead body 122 includes the insulation sheath 124 and insulation tubing 152 bounding the helical conductor 146. The helical conductor 146 may be made up of a plurality of conductors contained in a bundle 156 which are helically wound in a side-by-side manner. Each of the conductors contained in the bundle 156 may be individually coated or wrapped with an insulation material 158. In addition, a second conductor 148, which is also helically wound, is disposed internally of the insulation tubing 152.

As depicted in FIG. 5, a flexible insulative material 170, such as a silicone elastomer medical adhesive, has been interposed into the area bounded by the insulation sheath 124 and insulation tubing 152 to essentially encase the conductor 146 in the flexible insulative material 170. The flexible insulative material 170 thus coats and encapsulates the conductor 146 to the insulation tubings. The flexible insulative material 170 occupies the empty spacing between the insulation sheath 124 and insulation tubing 152.

The flexible insulative material 170 may be introduced in various ways, one of which could be by an injection process utilizing a syringe type of needle (not shown) which pierces the insulation sheath 124. The flexible insulative material is introduced while in a liquid state, and allowed to flow about the conductor 146. Following introduction, the flexible insulative material 170 solidifies, sealing the needle puncture of the insulation sheath 124. The flexible insulative material 170 increases the structural strength of the lead body 122 and, in particular, the conductor coil 146, and prevents localized bending, particularly sharp bending deformation, coil distortion, or compression of the conductor 146. The flexible insulative material 170 may be selected from the materials including silicone medical adhesive, silicone rubber, and polyurethane.

As illustrated in FIG. 5, the result of the inclusion of the flexible insulative material 170 is that the constriction forces applied by the first ribs 70 and clavicle 72 results in reduced distortion of the lead body 122, as compared to the construction illustrated in FIGS. 3 and 4. While the lead body 122 has enhanced structural stability, it still remains flexible due to the properties of the flexible insulative material which do not significantly impact the overall flexibility of the lead body 122.

The portion of the lead body 122 having the flexible insulative material 170 is long enough to be ultimately implanted and positioned to extend through and beyond the rib-clavicle area in a subclavian vein transvenous implant. In the preferred embodiment, the diameter of the lead body is in the range of between about 1.50 mm and 3.50 mm and preferably about 2.5 mm.

Figure 7:
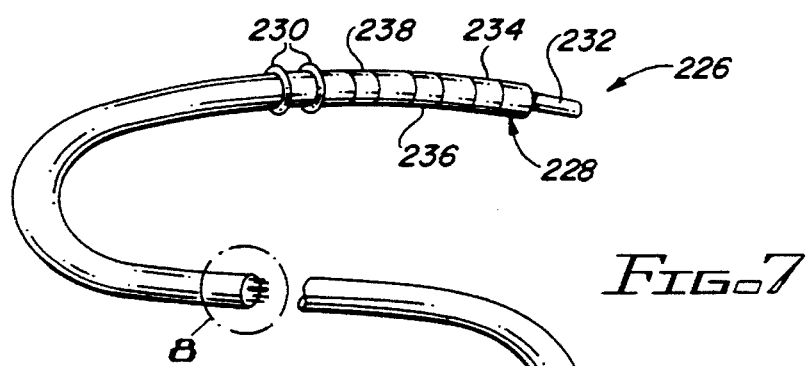
FIG. 7 shows a multilumen pacing lead.

FIG. 7 shows an alternative embodiment depicting a multilumen pacing lead 220 according to the present invention. The multilumen pacing lead 220 has an elongated lead body 222 which includes electrical conductors extending through lumens within a multilumen tubing 224. The multilumen tubing 224 is preferably fabricated of silicon, rubber, polyurethane, or another suitable plastic material having the properties of biocompatibility, biostability and flexibility.

At a proximal end 226 of the pacing lead 220 is a connector assembly 228, which is provided with sealing rings 230 and which includes electrical connectors 232, 234, 236 and 238. The portions of the connector assembly 228 spacing apart the connectors 234, 236, and 238 may be fabricated from segments of multilumen tubing of silicone, rubber, polyurethane, or other suitable plastic, assembled in the manner discussed herein below. The electrical connectors 232, 234, 236 and 238 are preferably fabricated of stainless steel or other suitable conductive material.

At a distal end 240 of the pacing lead 220 is an electrode assembly 242. A tip electrode 250 is located at the distal end 240 of the electrode assembly 242. A number of ring electrodes 252, 254, and 256 are shown spaced proximally from the distal end 240 of the pacing lead 220. The ring electrode 252 may be used, for example, as a cathode in a bipolar pacing system. Alternatively, the electrodes 252, 254 and 256 can be used as sensor electrodes to determine various parameters of endocardial activity, such as atrial electrical activity, ventricular electrical activity, or to sense impedance changes to determine stroke volume, pre-ejection fraction, and respiratory rate. Monitoring of these parameters is beneficial for advanced pacing systems to allow the pacemaker to more effectively control the cardiac activity.

Figure 8:
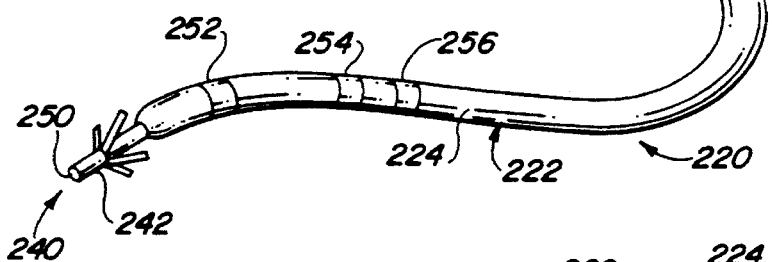
FIG. 8 depicts a partially cross-sectional perspective view of the multilumen pacing lead of FIG. 7 incorporating the present invention.
Figure 8:
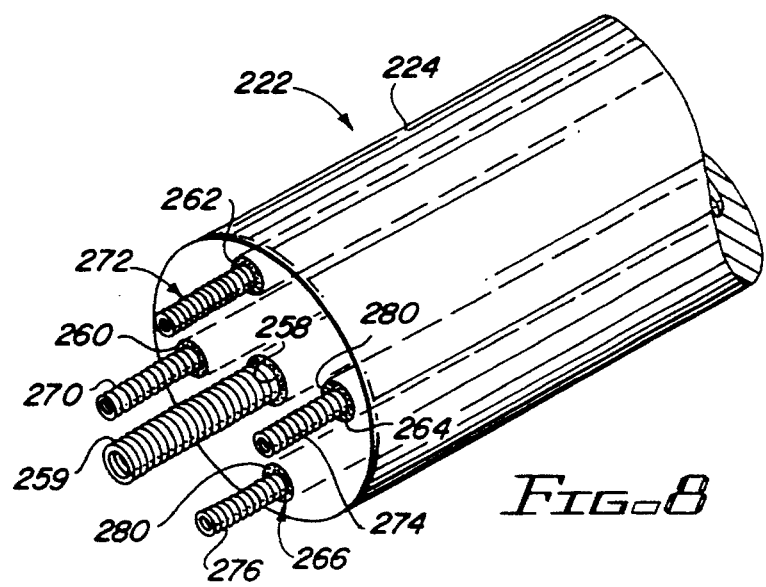

As shown in FIG. 8, the multilumen tubing 224 has a generally cylindrical cross-section with a central axial lumen 258 for receiving the conductor coil 259, and four lumens 260, 262, 264 and 266, which are spaced apart and axially aligned to extend along the length of the multilumen tubing 224. The lumens 260, 262, 264 and 266 provide enclosed pathways for electrical conductors 270, 272, 274 and 276. The electrical conductors 270, 272, 274 and 276 are preferably helical coils which, when inserted through the respective lumens 260, 262, 264, 266, each define an internal chamber or passageway.

Each of the lumens 260, 262, 264 and 266 is filled with a flexible material 280. This flexible material 280 is the same material as described above for FIGS. 5 and 6. The flexible material 280 may be introduced after the multilumen lead 220 has been assembled, for example by injection with a needle, or it can be introduced during assembly of the lead body 222. The flexible material minimizes the helical conductors 270, 272, 274 and 276 from being damaged by filling the internal chamber or passageway within each conductor 270, 272, 274 and 276.

It should be evident from the foregoing description that the present invention provide advantages over pacing leads of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. A method of preventing fatigue and tensile mechanical damage to conductors in a pacing lead having a lead body wherein the conductors are protected within an insulation sheath extending between and interconnecting a connector at a proximal end and an electrode at a distal end, comprising:
   a) assembling said pacing lead; and
   b) injecting a flexible insulative material into the insulation sheath, whereby said flexible insulative material surrounds the conductors.

2. A method of preventing fatigue and tensile mechanical damage to conductors in a pacing lead, as claimed in claim 1, wherein said flexible insulative material is selected from the group of materials consisting of silicone medical adhesive, silicone rubber, and polyurethane.

3. A method of preventing fatigue and tensile mechanical damage to conductors in a pacing lead having a lead body wherein at least one conductor is protected within an insulation sheath extending between and interconnecting a connector at a proximal end and an electrode at a distal end, comprising:
   a) assembling said pacing lead; and
   b) injecting a flexible insulative material into the insulation sheath, whereby said flexible insulative material surrounds a portion of the at least one conductor.

4. A method of preventing fatigue and tensile mechanical damage to conductors in a pacing lead, as claimed in claim 3, wherein said injecting step further comprises injecting said flexible insulative material such that the at least one conductor is surrounded by said flexible insulative material from a point near the proximal end of the lead to a point distal to the patient's ribs.

5. A method of preventing fatigue and tensile mechanical damage to conductors in a pacing lead, as claimed in claim 3, wherein said flexible insulative material is selected from the group of materials consisting of silicone medical adhesive, silicone rubber, and polyurethane.

6. A method of preventing fatigue and tensile mechanical damage to conductors in a pacing lead having a lead body wherein said lead body has a plurality of lumens and a plurality of conductors, each one of the plurality of conductors extending through a respective one of said lumens, wherein each conductor extends between and interconnects a connector at a proximal end and an electrode at a distal end, comprising:
   a) assembling said pacing lead; and
   b) injecting a flexible insulative material into at least one of said plurality of lumens, whereby said flexible insulative material surrounds a portion of the respective at least one of said plurality of conductors.

7. A method of preventing fatigue and tensile mechanical damage to conductors in a pacing lead, as claimed in claim 6, wherein said injecting step further comprises injecting said flexible insulative material such that the at least one of said plurality of conductors is surrounded by said flexible insulative material from a point near the proximal end of the lead to a point distal to the patient's ribs.

8. A method of preventing fatigue and tensile mechanical damage to conductors in a pacing lead, as claimed in claim 6, wherein said flexible insulative material is selected from the group of materials consisting of silicone medical adhesive, silicone rubber, and polyurethane.

* * * * *